United States Patent [19]

Gargiulo

[11] Patent Number: Plant 5,833

[45] Date of Patent: Dec. 16, 1986

[54] GRAPEVINE, "EMPERATRIZ"

[75] Inventor: Angelino A. Gargiulo, Mendoza, Argentina

[73] Assignees: Milan M. Caratan; Luis M. Caratan, both of Delano, Calif.

[21] Appl. No.: 682,110

[22] Filed: Dec. 11, 1984

[51] Int. Cl.[4] ..... A01H 5/03

[52] U.S. Cl. ..... Plt./47

[58] Field of Search ..... Plt./47

[56] References Cited

U.S. PATENT DOCUMENTS

P.P. 311 1/1939 Mkhalian .

*Primary Examiner*—Robert E. Bagwill

*Attorney, Agent, or Firm*—Worrel & Worrel

[57] ABSTRACT

A grapevine particularly characterized by its grapes which are generally similar to those of the Emperor (unpatented) grapevine having the late ripening, color, flavor and storage characteristics of the Emperor from which it is distinguished by a marked ability to benefit from the application of gibberellic acid thereon to improve the size and quality of the berries and which displays the seedless characteristics of the Thompson seedless grapevine.

1 Drawing Figure

BACKGROUND OF THE NEW VARIETY

The present invention relates to a new and distinct variety of grapevine to be known as the Emperatriz and more particularly to a grapevine which is generally similar to the Emperor (unpatented) grapevine but from which it is distinguished in several significant respects subsequently described.

The well-known Emperor grapevine has long been known as one of the best late bearing grapevines. Its fruit has desired color and stores and ships well when refrigerated. These and other characteristics have insured the Emperor grapevine an important place in the late marketing of grapes.

A substantial part of the applicant's professional life has been devoted to the creation of new and distinct varieties of grapevines. The present variety resulted from such efforts. The applicant has regularly selected grapevines having desired characteristics and cross-pollinated the selected grapevines to produce progeny of improved characteristics. For example, in the creation of the instant variety of grapevine, an object of the present invention was to perpetuate the desirable characteristics of the Emperor grapevine and the Thompson seedless (unpatented) grapevine.

Another object was to provide a grapevine having the late ripening, good color, excellent flavor, excellent storage and shipping characteristics of the Emperor grapevine and the seedless characteristics of the Thompson seedless grapevine. Further, it is the usual practice to apply gibberellic acid to grapevines intended to produce fresh grapes in order to improve the size and quality of the berries. It has long been known that the application of gibberellic acid to Emperor grapevines has slight effect but application thereof to Thompson seedless grapevines has a very marked ability to increase the size and quality of the berries. Another object was, therefore, to produce a new variety of grapevine which has the desirable characteristics of the Emperor grapevine and at the same time is susceptible to gibberellic acid to improve the size and quality of the berries.

ORIGIN AND ASEXUAL REPRODUCTION OF THE NEW VARIETY

The applicant cross-pollinated an Emperor grapevine with a Thompson seedless grapevine at a test plot near Rama, Caida, Argentina. The resultant progeny were grown to an extent sufficient to determine their characteristics. The subject variety was selected by the applicant for its desirable characteristics and asexually reproduced by the applicant by budding into host grapevines and by rooting cuttings. In both instances the characteristics of the grapevines resulting from such asexual reproduction proved identical to those of the original hybrid.

SUMMARY OF THE NEW VARIETY

The subject variety of grapevine is best characterized by its perpetuation of the desirable characteristics of the Emperor grapevine but displays the important distinctions of ripening approximately seven days earlier than the Emperor grapevine grown under the same cultural and climatic conditions. The new variety is seedless. The new variety is highly susceptible to the desirable effects of gibberellic acid.

In many instances, if untreated by gibberellic acid, the subject variety and the regular Emperor display substantially identical coloration, the same loose bunches with a very wide variety of berry sizes while if they are grown under substantially identical conditions but both treated with gibberellic acid, the regular Emperor displays virtually no beneficial results of the gibberellic acid while the grapevine of the instant application treated with gibberellic acid is particularly characterized by the uniformity in size, color and shape of the resultant berries.

BRIEF DESCRIPTION OF THE DRAWING

The accompanying drawing is a color photograph of a bunch of grapes of the subject variety and a pair of characteristic leaves thereof showing their front and back sides.

DETAILED DESCRIPTION

Referring more specifically to the pomological details of the new and distinct variety of grapevine, the following has been observed under the ecological conditions prevailing in the applicant's test plot near Rama, Caida, Argentina.

All major color code plate identifications having parenthetical numerals are by reference to the *Dictionary of Color* by A. Maerz and M. Paul, Second Edition, published in 1950. Where the color code plate identification is beyond the range of such dictionary, common color names are used and no code identification numerals parenthetically provided.

VINE

Size: Large.
Growth: Vigorous.
Productivity: Heavy, regular bearer.
Canes: Stout
*Joints.*—Spaced more than usual.
*Tendrils.*—Short, scarce, delicate.
*Color.*—Light green (23-9).
Growing tip: Woolly, green (23-9), without red-carmine (31-13) halo characteristics of Emperor grapevine.
Herbaceous stem: Glabrous, slightly red-carmine (31-13).

FOLIAGE

Upper young leaves: With cobwebby indument in both sides of the leaf, more intense on the underside.
Lower young leaves: Contorted; glabrous in the upper surface and cobwebby in the lower surface with a copper hue (30-12) diffused on the upper surface.
Mature leaf: Very contorted, with tendency to involute; large; orbicular; smooth light green (22-11), a bit glossy, medium five-lobed, with lower lobes inconspicuous.
Indument: Almost glabrous.
Petiolar sinus: "V" shape; narrow; the lower lobes partially overlapping, giving the impression of holes punched in the leaves.
Petiolar junction: The base of the veins intensely colored of violet red hue.

BLOSSOMS

Blooms: March 15 to March 24 in the Northern Hemisphere and September 15 to September 24 in the Southern Hemisphere.
Flowers: Abundant.
*Length of blooming season.*—Approximately ten days.
*Color.*—The same as the well-known Emperor grapevine; principally white with slight green hue.
Reproductive organs: Medium to abundant.

FRUIT

Maturity in southern hemisphere: March 25.
Maturity in northern hemisphere: September 25.
Harvest in southern hemisphere: Mid March to mid June.
Harvest in northern hemisphere: Mid September to mid December.
Color: Pink to reddish (41-14) widely varied.
Shape: Ovoid.
Size of berries: Medium and widely varied unless treated with gibberellic acid.
Average diameters: 16 mm.
Average base to apex: 20 mm.
Average number of clusters to vine: 25.
Average number of berries to cluster: 300.
Number of seeds to berry: Average 2 soft seeds or "false seeds".
Productivity: Heavy.
Clusters ripen: Unevenly unless previously treated with gibberellic acid.
Aroma: Excellent.
Taste: With a touch of plum, not very sweet, acid, tasty.
Eating quality: Excellent.
Juice quality: Excellent.
Shipping and storing qualities: Excellent.
Uses: Fresh table grapes, raisins and wine.
General appearance: Excellent if first treated with gibberellic acid.
Climatic preference: Not recommended for cool regions because of short vegetative cycle.
Competition: Ripens when no other comparable grapevines ripen.

RAISINS MADE FROM SUBJECT VARIETY

General appearance: Good.
Color: Widely varied, from yellowish to light violet.
Shape: Substantially spherical but slightly elongated, ovoid.
Size: Medium.
Length: Medium, 13.1 mm.
Smallest: 11 mm.
Biggest: 16 mm. (average of 10 raisins).
Width: Medium, 9.8 mm.
Smallest: 8 mm.
Biggest: 12 mm. (average of 10 raisins).
Uniformity of size: Medium dispersion.
Weight of 100 raisins: 45.5 grams.
Skin consistency: Soft, leaves no residue when chewed.
Seed remnant: It is perceived in very few raisins.

Although the new variety of grapevine possesses the described characteristics as a result of the growing conditions prevailing in Rama, Caida, Argentina, it is to be understood that variations of the usual magnitude in characteristics incident to growing conditions, fertilization, pruning and pest control are to be expected.

Having thus described and illustrated my new variety of grapevine, I claim:

1. A new and distinct variety of grapevine to be known as the Emperatriz substantially as illustrated and described, characterized principally by its production of seedless berries which mature approximately a week earlier than those of the Emperor grapevine, which it most nearly resembles, but from which it is distinguished by the berries being somewhat smaller and more nearly spherical than the berries of the Emperor, looser bunches which are much more susceptible to the action of gibberellic acid to enlarge the berries and to fill out the bunches than is the Emperor which has little or no reaction to gibberellic acid.

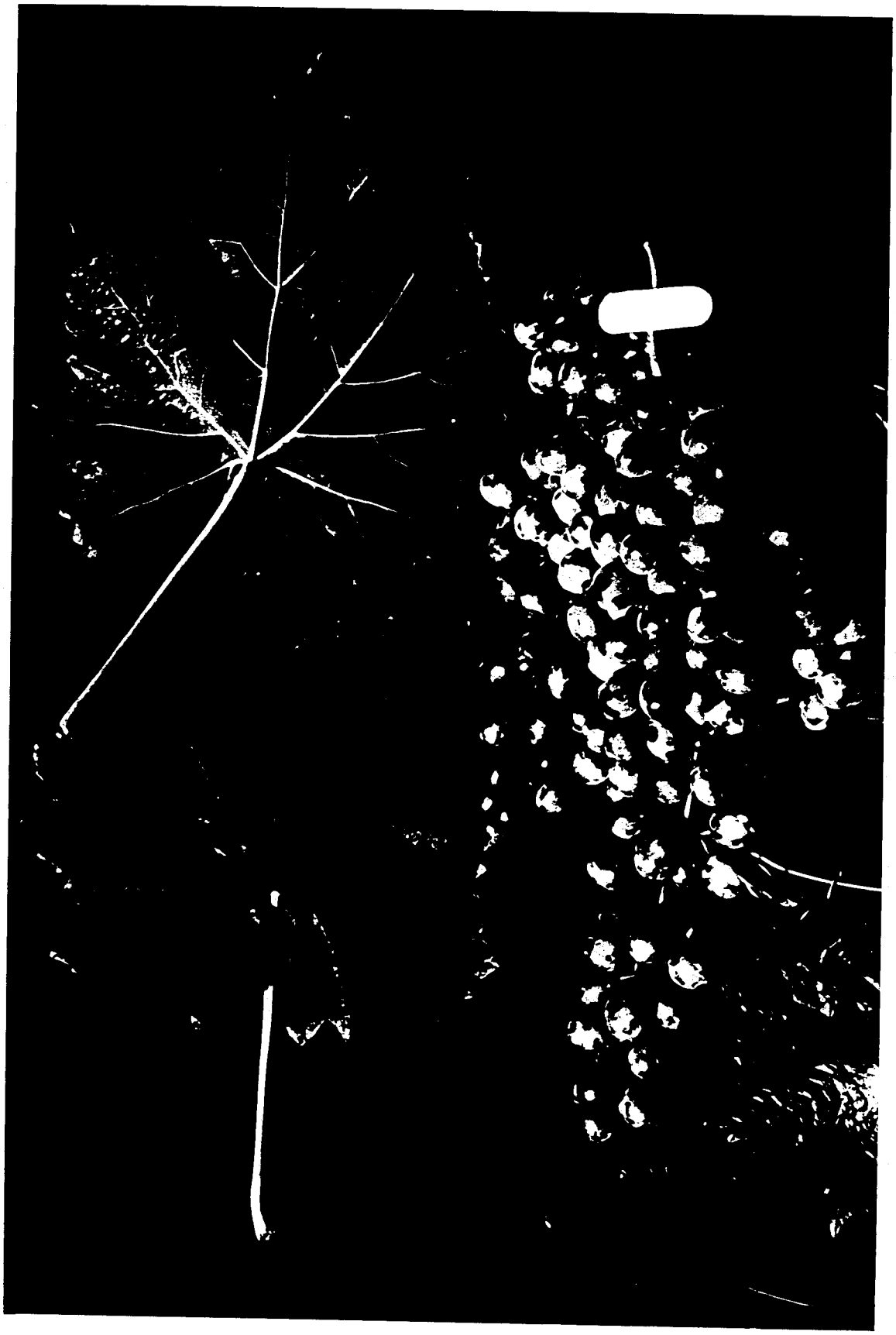

* * * * *